(12) United States Patent
Yook et al.

(10) Patent No.: US 11,709,193 B2
(45) Date of Patent: Jul. 25, 2023

(54) SIGNAL DETECTION CIRCUIT AND SENSOR WITH INTERFEROMETER CIRCUIT TO SENSITIVELY DETECT SMALL VARIATION IN SIGNAL SIZE

(71) Applicant: UIF (University Industry Foundation), Yonsei University, Seoul (KR)

(72) Inventors: Jonggwan Yook, Seoul (KR); Chorom Jang, Seoul (KR); Jinkwan Park, Seoul (KR)

(73) Assignee: UIF (University Industy Foundation), Yonsei University, Seoul (KR)

( * ) Notice: Subject to any disclaimer, the term of this patent is extended or adjusted under 35 U.S.C. 154(b) by 0 days.

(21) Appl. No.: 17/707,347

(22) Filed: Mar. 29, 2022

(65) Prior Publication Data

US 2022/0317170 A1     Oct. 6, 2022

(30) Foreign Application Priority Data

Apr. 1, 2021   (KR) .......................... 10-2021-0042710

(51) Int. Cl.

| | | |
|---|---|---|
| *G01R 27/04* | (2006.01) | |
| *G01R 27/32* | (2006.01) | |
| *G01R 29/08* | (2006.01) | |
| *G01N 22/00* | (2006.01) | |
| *G01N 22/04* | (2006.01) | |
| *G01N 27/02* | (2006.01) | |
| *A61B 5/00* | (2006.01) | |
| *A61B 5/05* | (2021.01) | |

(52) U.S. Cl.
CPC ......... *G01R 29/0892* (2013.01); *G01N 22/00* (2013.01); *G01N 22/04* (2013.01); *G01N 27/02* (2013.01); *A61B 5/0031* (2013.01); *A61B 5/05* (2013.01); *A61B 2560/0219* (2013.01)

(58) Field of Classification Search
CPC .... G01R 29/0892; G01R 27/28; G01R 27/04; G01N 22/00; G01N 33/49; G01N 22/04; G01N 27/02; A61B 5/0031; A61B 2560/0219; A61B 5/05
USPC ........... 324/76.11–76.83, 459, 600, 629, 633
See application file for complete search history.

(56) References Cited

U.S. PATENT DOCUMENTS

| | | | | |
|---|---|---|---|---|
| 2008/0204041 A1* | 8/2008 | Anderson | ............... | G01R 27/28 324/629 |
| 2010/0102828 A1* | 4/2010 | Bromberg | .......... | B01D 46/0086 324/639 |
| 2013/0181725 A1* | 7/2013 | Mazzaro | ................. | H01P 7/082 324/636 |

(Continued)

FOREIGN PATENT DOCUMENTS

| | | |
|---|---|---|
| JP | 2006-189392 A | 7/2006 |
| KR | 200322662 Y1 | 8/2003 |

OTHER PUBLICATIONS

JP 2006189392 Machine Translation, 2006-07-20 (Year: 2006).*

*Primary Examiner* — Raul J Rios Russo

(57) ABSTRACT

The present exemplary embodiments provide a signal detection circuit and a sensor which improve a quality factor of a resonator by modeling an initial state of the resonator using an attenuator and a phase shifter which are modeling paths and significantly change a transmission coefficient of the resonator even with a small variation of an object to be measured.

8 Claims, 4 Drawing Sheets

(56) References Cited

U.S. PATENT DOCUMENTS

2015/0293159 A1* 10/2015 van Bezooijen ..... H04B 1/0458
333/32
2018/0267087 A1* 9/2018 Nagasawa .............. G01R 27/04
2020/0166553 A1* 5/2020 Bloss ................. G01R 31/2822

* cited by examiner

SIGNAL DETECTION CIRCUIT AND SENSOR WITH INTERFEROMETER CIRCUIT TO SENSITIVELY DETECT SMALL VARIATION IN SIGNAL SIZE

CROSS-REFERENCE TO RELATED APPLICATIONS

This application claims priority to and the benefit of Korean Patent Application No. 10-2021-0042710 filed in the Korean Intellectual Property Office on Apr. 1, 2021, the entire contents of which are incorporated herein by reference.

TECHNICAL FIELD

The technical field of the present disclosure relates to an interferometer circuit to sensitively detect a small variation in a signal size. This study relates to the research project of the National Research Foundation of Korea funded by the Ministry of Education in 2021 (No. NRF-2021R1A6A3A13046764).

BACKGROUND ART

The contents described in this section merely provide background information on the present exemplary embodiment but do not constitute the related art.

According to a detecting method of the related art which uses a microwave resonator, an object to be detected is placed in a portion in which the strongest near-field of the resonator is formed and a variation amount of the signal due to interaction between the object and the near-field is detected. However, according to the related art, the sensitivity is low due to the low quality factor of the resonator so that it is difficult to be applied as a sensor for detecting a small variation.

RELATED ART DOCUMENT

Patent Document

Patent Document 1: KR 20-0322662 (2003 Jul. 30)

SUMMARY OF THE INVENTION

A main object of the exemplary embodiments of the present disclosure is to improve a quality factor of a resonator by modeling an initial state of the resonator using an attenuator and a phase shifter which are modeling paths and significantly change a transmission coefficient of the resonator even with a small variation of an object to be measured.

Other and further objects of the present invention which are not specifically described can be further considered within the scope easily deduced from the following detailed description and the effect.

According to an aspect of the present embodiment, a signal detection circuit includes a resonator connected to an object to be measured; and an interferometer circuit which is connected to the object to be measured and the resonator and models a size and a phase of a transmission coefficient of the resonator.

The interferometer circuit includes: an attenuator which is connected to the resonator in parallel and models the magnitude of the transmission coefficient of the resonator; and a phase shifter which is connected to the resonator and models the phase of the transmission coefficient of the resonator.

The interferometer circuit includes: a first hybrid coupler which is connected to the resonator and the attenuator and generates a 90-degree phase difference; and a second hybrid couple which is connected to the object to be measured and the phase shifter and generates a 90-degree phase difference.

The first hybrid coupler and the second hybrid coupler increase an isolation level between (i) a signal detection path according to the resonator and the object to be measured and (ii) a signal modeling path according to the attenuator and the phase shifter.

The first hybrid coupler and the second hybrid coupler allow a signal to have the same magnitude as a transmission signal of an initial resonator and have a 180-degree phase difference in (i) a signal detection path according to the resonator and the object to be measured and (ii) a signal modeling path according to the attenuator and the phase shifter.

The destructive interference is generated in (i) a signal detection path according to the resonator and the object to be measured and (ii) a signal modeling path according to the attenuator and the phase shifter.

According to another aspect of the present embodiment, a sensor includes a signal detection circuit including an interferometer circuit which is connected to an object to be measured and an resonator connected to the object to be measured and models a magnitude and a phase of a transmission coefficient of the resonator; and a controller which measures a magnitude of an electric signal output from the signal detection circuit to output whether to detect.

As described above, according to the exemplary embodiments of the present disclosure, a magnitude and a phase of a transmission coefficient of the resonator are modeled using an attenuator and a phase shifter and an isolation level between paths is increased using a plurality of hybrid couplers and signals are interfered according to the path to detect a small change in a signal by a large variation of the transmission coefficient.

The exemplary embodiments of the present disclosure may be utilized as a noninvasive blood glucose meter.

Even if the effects are not explicitly mentioned here, the effects described in the following specification which are expected by the technical features of the present disclosure and their potential effects are handled as described in the specification of the present disclosure.

DETAILED DESCRIPTION OF THE EMBODIMENT

Hereinafter, in the description of the present disclosure, a detailed description of the related known functions will be omitted if it is determined that the gist of the present disclosure may be unnecessarily blurred as it is obvious to those skilled in the art and some exemplary embodiments of the present disclosure will be described in detail with reference to exemplary drawings.

Figure 1:
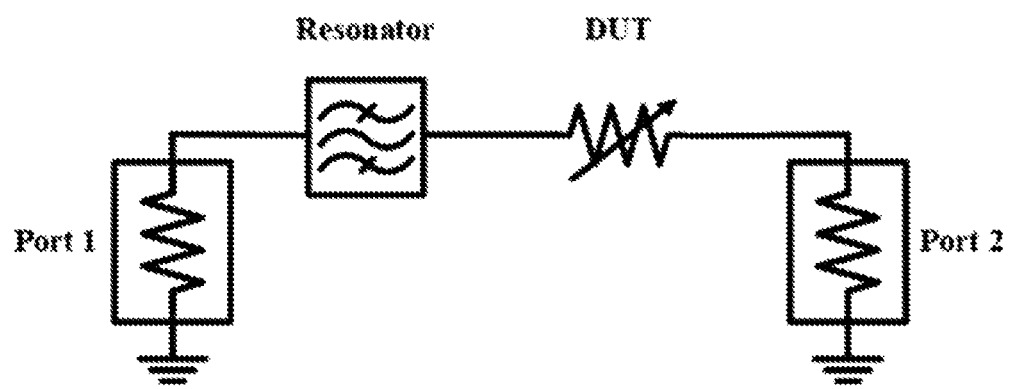
FIG. 1 is a view illustrating a signal detection circuit using a resonator of the related art.

FIG. 1 is a view illustrating a signal detection circuit using a resonator of the related art. The circuit illustrated in FIG. 1 detects a change of a resistance using a microwave resonator.

According to the existing method using a microwave resonator, an object to be detected is placed in a portion where a strongest near-field of the resonator is formed and a variation thereof is detected. However, according to this method, the sensitivity is low due to the low quality factor of the resonator so that it is difficult to be developed as a sensor for detecting a small variation.

In order to improve this problem, according to the present disclosure, an interferometer circuit is designed and an initial state of the resonator is modeled using an attenuator and a phase shifter which are modeling paths to improve a quality factor of the resonator. Therefore, the transmission coefficient of the resonator significantly changes even with a small variation of an object to be analyzed.

Figure 2:
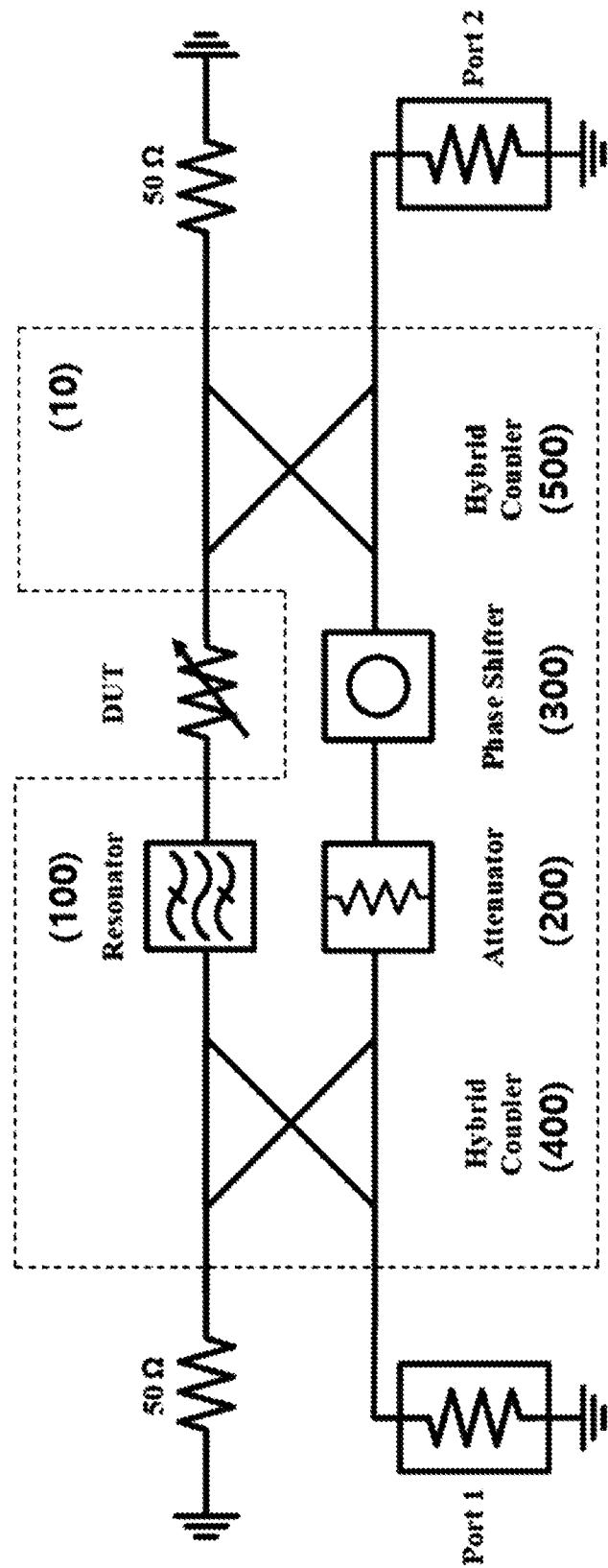
FIG. 2 is a view illustrating a signal detection circuit to which an interferometer circuit according to an exemplary embodiment of the present disclosure is applied.

FIG. 2 is a view illustrating a signal detection circuit to which an interferometer circuit according to an exemplary embodiment of the present disclosure is applied.

The signal detection circuit according to the exemplary embodiment improves the sensitivity by coupling the microwave resonator and the interferometer circuit. The signal detecting circuit according to the present exemplary embodiment models the magnitude and the phase of the transmission coefficient of the resonator using an attenuator and a phase shifter and an isolation level between paths is increased using a plurality of hybrid couplers, and the signal according to the path is interfered to detect a small change in the signal by a large variation of the transmission coefficient. The interferometer circuit is applied so that sensitivity may be improved more than a case that uses only a microwave resonator.

The signal detection signal according to the present exemplary embodiment detects even a small change so that it may be developed to a sensor which detects a blood glucose which has a small change in an electrical characteristic according to a concentration. The method for improving a sensitivity of the sensor is applicable to various measurement methods such as electrical and electronic engineering, bio fusion fields, and medical device fields.

The signal detection circuit combined with the interferometer circuit illustrated in FIG. 2 models a magnitude and a phase of a transmission coefficient of the microwave resonator using an attenuator and a phase shifter. Two 90-degree hybrid couplers are connected to an input port and an output port to divide and combine signals while increasing an isolation level between a detection path and a modeling path so that two signal paths have the same magnitude and 180-degree phase difference. By doing this, the output port of the system has a very small size due to the destructive interference of signals of two paths and the change in the variable resistance can be more sensitively detected.

The signal detection circuit 10 includes a resonator 100 and an interferometer circuit. The resonator 100 is connected to an object to be measured. The interferometer circuit is connected to the object to be measured and the resonator 100 and models the magnitude and the phase of the transmission coefficient of the resonator.

The interferometer circuit includes an attenuator 200, a phase shifter 300, a first hybrid coupler 400, and a second hybrid coupler 500.

The attenuator 200 is connected to the resonator 100 in parallel and models the magnitude of the transmission coefficient of the resonator 100.

The phase shifter 300 is connected to the attenuator 200 and models a phase of the transmission coefficient of the resonator 300.

The first hybrid coupler 400 is connected to the resonator 100 and the attenuator 200 and generates a 90-degree phase difference.

The second hybrid coupler 500 is connected to the object to be measured and the phase shifter 300 and generates a 90-degree phase difference.

The first hybrid coupler 400 and the second hybrid coupler 500 may increase an isolation level between (i) a signal detection path according to the resonator and the object to be measured and (ii) a signal modeling path according to the attenuator and the phase shifter.

The first hybrid coupler 400 and the second hybrid coupler 500 may allow the signal to have the size the same as the transmissive signal of the initial resonator and have 180-degree phase difference in (i) the signal detection path according to the resonator and the object to be measured and (ii) the signal modeling path according to the attenuator and the phase shifter. The destructive interference may be generated in (i) the signal detection path according to the resonator and the object to be measured and (ii) the signal modeling path according to the attenuator and the phase shifter.

Figure 3:
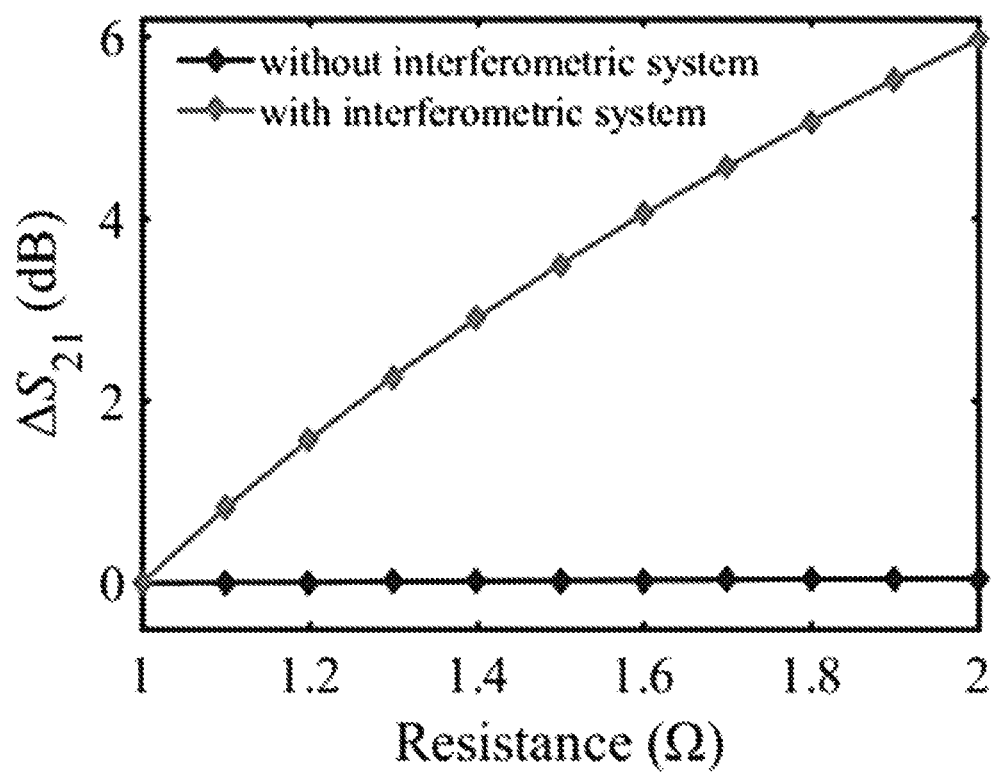
FIG. 3 is a view illustrating a simulation result according to an exemplary embodiment of the present disclosure.

FIG. 3 is a result graph obtained by simulating a variation in a transmission coefficient when a variable resistance is changed from 1Ω to 2Ω with respect to a circuit in which a general detection using a resonator and the interferometer circuit are coupled.

It is confirmed that when the interferometer circuit according to the exemplary embodiment is coupled, as compared with the detection circuit without having the interferometer circuit, the change in a signal size due to the change in the resistance may be sensitively detected.

Figure 4:
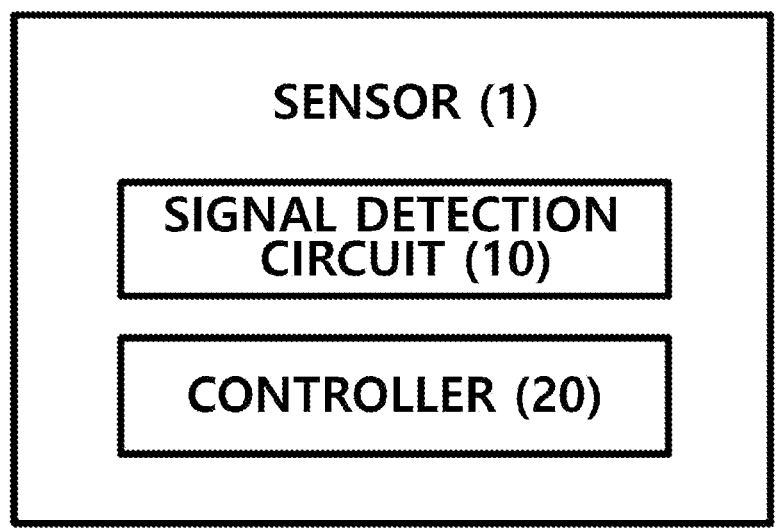
FIG. 4 is a view illustrating a sensor according to another exemplary embodiment of the present disclosure.

FIG. 4 is a view illustrating a sensor according to another exemplary embodiment of the present disclosure.

A sensor 1 includes a signal detection signal 10 including an interferometer circuit which is connected to an object to be measured and a resonator connected to the object to be measured and models a magnitude and a phase of a transmission coefficient of the resonator. The sensor 1 includes a controller 20 which measures an intensity of an electric signal output from the signal detection circuit 10 to output whether to detect.

The controller 20 includes a microprocessor and an analog digital converter and measures an intensity of the electric signal and outputs whether to detect according to a result of comparing the intensity of the electric signal with a reference value. The electric signal is a current or voltage signal. The controller 20 calculates a resistance according to a relational equation for a current or a voltage.

A plurality of components included in various electronic devices to which the sensor is applied is coupled to each other to be implemented by at least one module. The components are connected to a communication path which connects a software module or a hardware module in the apparatus to organically operate between the components. The components communicate with each other using one or more communication buses or signal lines.

The various electronic devices to which the sensor is applied may be implemented in a logic circuit by hardware, firm ware, software, or a combination thereof or may be implemented using a general purpose or special purpose computer. The sensor may be implemented using hardwired device, field programmable gate array (FPGA) or application specific integrated circuit (ASIC). Further, the sensor may be implemented by a system on chip (SoC) including one or more processors and a controller.

The various electronic devices to which the sensor is applied may be mounted in a computing device provided with a hardware element as a software, a hardware, or a combination thereof. The computing device may refer to various devices including all or some of a communication device for communicating with various devices and wired/wireless communication networks such as a communication modem, a memory which stores data for executing programs, and a microprocessor which executes programs to perform operations and commands.

The present embodiments are provided to explain the technical spirit of the present embodiment and the scope of the technical spirit of the present embodiment is not limited by these embodiments. The protection scope of the present embodiments should be interpreted based on the following appended claims and it should be appreciated that all technical spirits included within a range equivalent thereto are included in the protection scope of the present embodiments.

What is claimed is:

1. A signal detection circuit, comprising:
   a resonator connected to an object to be measured; and
   an interferometer circuit which is connected to the object to be measured and the resonator and models a magnitude and a phase of a transmission coefficient of the resonator,
   wherein the interferometer circuit includes:
      an attenuator which is connected to the resonator in parallel and models the magnitude of the transmission coefficient of the resonator;
      a phase shifter which is connected to the resonator and models the phase of the transmission coefficient of the resonator;
      a first hybrid coupler which is connected to the resonator and the attenuator and generates a 90-degree phase difference; and
      a second hybrid coupler which is connected to the object to be measured and the phase shifter and generates a 90-degree phase difference.

2. The signal detection circuit according to claim 1, wherein the first hybrid coupler and the second hybrid coupler increase an isolation level between (i) a signal detection path according to the resonator and the object to be measured and (ii) a signal modeling path according to the attenuator and the phase shifter.

3. The signal detection circuit according to claim 1, wherein the first hybrid coupler and the second hybrid coupler allow a signal to have the same magnitude as a transmission signal of an initial resonator and have a 180-degree phase difference in (i) a signal detection path according to the resonator and the object to be measured and (ii) a signal modeling path according to the attenuator and the phase shifter.

4. The signal detection circuit according to claim 1, wherein destructive interference is generated in (i) a signal detection path according to the resonator and the object to be measured and (ii) a signal modeling path according to the attenuator and the phase shifter.

5. A sensor, comprising:
   a signal detection circuit including an interferometer circuit which is connected to an object to be measured and a resonator connected to the object to be measured and models a magnitude and a phase of a transmission coefficient of the resonator; and
   a controller which measures a magnitude of an electric signal output from the signal detection circuit to output whether to detect,
   wherein the interferometer circuit includes:
      an attenuator which is connected to the resonator in parallel and models the magnitude of the transmission coefficient of the resonator;
      a phase shifter which is connected to the resonator and models the phase of the transmission coefficient of the resonator;
      a first hybrid coupler which is connected to the resonator and the attenuator and generates a 90-degree phase difference; and
      a second hybrid coupler which is connected to the object to be measured and the phase shifter and generates a 90-degree phase difference.

6. The sensor according to claim 5, wherein the first hybrid coupler and the second hybrid coupler increase an isolation level between (i) a signal detection path according to the resonator and the object to be measured and (ii) a signal modeling path according to the attenuator and the phase shifter.

7. The sensor according to claim 5, wherein the first hybrid coupler and the second hybrid coupler allow a signal to have the same magnitude as a transmission signal of an initial resonator and have a 180-degree phase difference in (i) a signal detection path according to the resonator and the object to be measured and (ii) a signal modeling path according to the attenuator and the phase shifter.

8. The sensor according to claim 5, wherein destructive interference is generated in (i) a signal detection path according to the resonator and the object to be measured and (ii) a signal modeling path according to the attenuator and the phase shifter.

* * * * *